United States Patent
Tucker et al.

(10) Patent No.: US 9,744,200 B1
(45) Date of Patent: Aug. 29, 2017

(54) SYSTEM FOR PRODUCING A TERPENE-ENHANCED CANNABINOID CONCENTRATE

(71) Applicant: Oak and Crane, LLC, Hayfork, CA (US)

(72) Inventors: Gary Tucker, Hayfork, CA (US); William Lee Fulton, Oregon City, OR (US)

(73) Assignee: Oak and Crane, LLC, Hayfork, CA (US)

( * ) Notice: Subject to any disclaimer, the term of this patent is extended or adjusted under 35 U.S.C. 154(b) by 0 days.

(21) Appl. No.: 15/477,668

(22) Filed: Apr. 3, 2017

Related U.S. Application Data (63) Continuation-in-part of application No. 15/410,289, filed on Jan. 19, 2017, now Pat. No. 9,649,349.

(51) Int. Cl.
| | |
|---|---|
| *A01N 65/00* | (2009.01) |
| *A61K 36/18* | (2006.01) |
| *A23L 27/10* | (2016.01) |
| *B01D 11/02* | (2006.01) |
| *B01D 3/14* | (2006.01) |

(52) U.S. Cl.
CPC ............ *A61K 36/18* (2013.01); *A23L 27/10* (2016.08); *B01D 3/143* (2013.01); *B01D 11/0203* (2013.01); *A23V 2002/00* (2013.01); *A61K 2236/15* (2013.01); *A61K 2236/33* (2013.01); *A61K 2236/37* (2013.01); *A61K 2236/39* (2013.01); *A61K 2236/50* (2013.01); *A61K 2236/51* (2013.01); *A61K 2236/55* (2013.01)

(58) Field of Classification Search
CPC ...................................................... A61K 36/00
USPC ........................................................... 424/725
See application file for complete search history.

(56) References Cited

U.S. PATENT DOCUMENTS

2016/0324091 A1  11/2016  Lewis et al.

FOREIGN PATENT DOCUMENTS

CA      2911168 A1    5/2015

*Primary Examiner* — Michael Meller
(74) *Attorney, Agent, or Firm* — Arc IP Law, PC; Joseph J. Mayo (57) ABSTRACT

A system for producing a blended extract of cannabinoids and terpenes, which extracts terpenes using supercritical CO2, and extracts a cannabinoid concentrate from the residual material using a cold ethanol flush followed by distillation; the CO2-extracted terpenes are then added back to the cannabinoid concentrate in a final blending step. Blending terpenes at the end of extraction may enhance the flavor and effectiveness of the cannabinoid concentrate. By separately extracting terpenes and cannabinoids, optimal processes and parameters may be used for each step. Blending may combine terpenes and cannabinoids in any desired ratio; for example, a terpene-to-cannabinoid ratio of approximately 1:10 may be used. The ethanol used in the cold ethanol extraction of cannabinoids may be recovered and reused for subsequent batches. Cannabinoid concentrates may be redistilled multiple times to enhance their concentration, followed by terpene blending.

17 Claims, 10 Drawing Sheets

SYSTEM FOR PRODUCING A TERPENE-ENHANCED CANNABINOID CONCENTRATE

This application is a continuation-in-part of U.S. Utility patent application Ser. No. 15/410,289 filed 19 Jan. 2017, the specification of which is hereby incorporated herein by reference.

BACKGROUND OF THE INVENTION

Field of the Invention

One or more embodiments of the invention are related to the field of extraction of substances from plant material. More particularly, but not by way of limitation, one or more embodiments of the invention enable a system for producing a terpene-enhanced cannabinoid concentrate from *cannabis* plant material.

Description of the Related Art

Several methods for extracting cannabinoids from *cannabis* plant material are known in the art. A limitation of many of these methods is that the terpenes in the *cannabis* plant are often lost or greatly reduced in the final extracted product. While cannabinoids provide a major element of the medicinal or psychoactive effect of *cannabis*, the many terpenes in the *cannabis* plant also contribute significantly to the plant's properties.

*Cannabis* processors have explored techniques to simultaneously extract cannabinoids and preserve terpenes, with limited success. Processes and parameters that are optimal for cannabinoid extraction may be ineffective for terpene extraction, and vice-versa. Moreover, tuning the ratio of terpenes to cannabinoids is difficult or impossible when attempting to extract both simultaneously. A potential solution to these difficulties, which is not known in the art, is to combine separate procedures for terpene extraction and *cannabis* extraction, and to blend the outputs of these procedures into a final product. This approach allows optimal processes and parameters to be used for each step, and it provides maximum flexibility for the composition of the final blend. There are no known methods that use such an approach to generate a terpene-enhanced cannabinoid concentrate. In addition, the only method known in the art for terpene extraction is steam distillation, which extracts a limited profile of terpenes because it is water based. There is a need for combining a more effective terpene extraction process with a blending process that combines terpenes and cannabinoids.

For at least the limitations described above there is a need for a system for producing a terpene-enhanced cannabinoid concentrate.

BRIEF SUMMARY OF THE INVENTION

One or more embodiments described in the specification are related to a system for producing a terpene-enhanced cannabinoid concentrate. Embodiments of the invention combine an extraction process for terpene oil and an extraction process for cannabinoids, to yield a blend with combined benefits of terpenes and cannabinoids.

One or more embodiments of the invention may produce a terpene-enhanced cannabinoid concentrate using the following steps: *Cannabis* plant material is ground, then exposed to a carbon dioxide solvent, for example using a supercritical $CO_2$ fluid. The $CO_2$ extracts terpene oil and terpene hydrosols from the *cannabis*. The residual plant material (after $CO_2$ extraction) is then washed with cold ethanol, and the resulting ethanol oil solution is separated into ethanol (which may be recycled) and *cannabis* oil. The *cannabis* oil is then distilled to obtain cannabinoid distillates. These cannabinoid distillates are blended with the terpene oil from $CO_2$ extraction, yielding a terpene-enhanced cannabinoid concentrate. Terpenes may for example add flavor to the cannabinoid concentrate or enhance the effects of the concentrate.

Cannabinoid distillates may include any or all of THC, CBD, CBG, CBN, and THCV. In one or more embodiments, the concentration of cannabinoids in the cannabinoid distillates may be 80% or higher. The cannabinoid distillates may be optionally redistilled (multiple times if desired) to increase the cannabinoid concentration.

Terpenes extracted in the terpene oil and terpene hydrosols may include any or all of alpha-Bisabolol, Camphene, 3-Carene, beta-Caryophyllene, Citronellol, Cymene, Eucalyptol, Famesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene.

Terpene oil and cannabinoid concentrate may be combined in any ratio. In one or more embodiments, the ratio by volume of terpene oil to cannabinoid concentrate may be in the range of 1:25 to 1:5. In one or more embodiments the ration may be in the range of 1:12 to 1:8. As an illustration, one or more embodiments may generate a blend with a terpene-to-cannabinoid concentrate ratio of approximately 1:10.

Illustrative parameters used for $CO_2$ extraction of terpene oil and terpene hydrosol in one or more embodiments may include for example: $CO_2$ pressure in the range of 1000 psi to 1300 psi, forming a supercritical fluid; temperature between 80 F and 100 F; and elapsed time of exposing the *cannabis* plant material to the supercritical $CO_2$ in the range of 15 minutes to 6 hours. After $CO_2$ extraction and removal of $CO_2$ (for example by reducing pressure to allow the $CO_2$ to evaporate), the terpene oil and terpene hydrosol may be filtered at a temperature between −80 F and 40 F, using a filter with pore size greater than 0.25 micron.

Illustrative parameters used for cold ethanol extraction and ethanol recovery in one or more embodiments may include for example: flushing of residual plant material with cold ethanol at a temperature of 30 F or below; and distilling the ethanol oil solution at a temperature between 120 F and 165 F under a vacuum between 10 inches Hg and 25 inches Hg. Recovered ethanol may be optionally reused for subsequent washing of a second batch of material.

Distilling of *cannabis* oil into cannabinoid distillates may be performed in one or more embodiments under vacuum with a pressure at or below 5 torr. Cannabinoid distillates may be obtained at a temperature of between 157 C and 230 C. In one or more embodiments, distillation may also yield terpene distillates, for example at a temperature between 140 C and 157 C. Distillation of these products may be performed multiple times to increase concentration or purity, followed by blending of terpene oil with the cannabinoid distillates.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A system for producing a terpene-enhanced cannabinoid concentrate will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
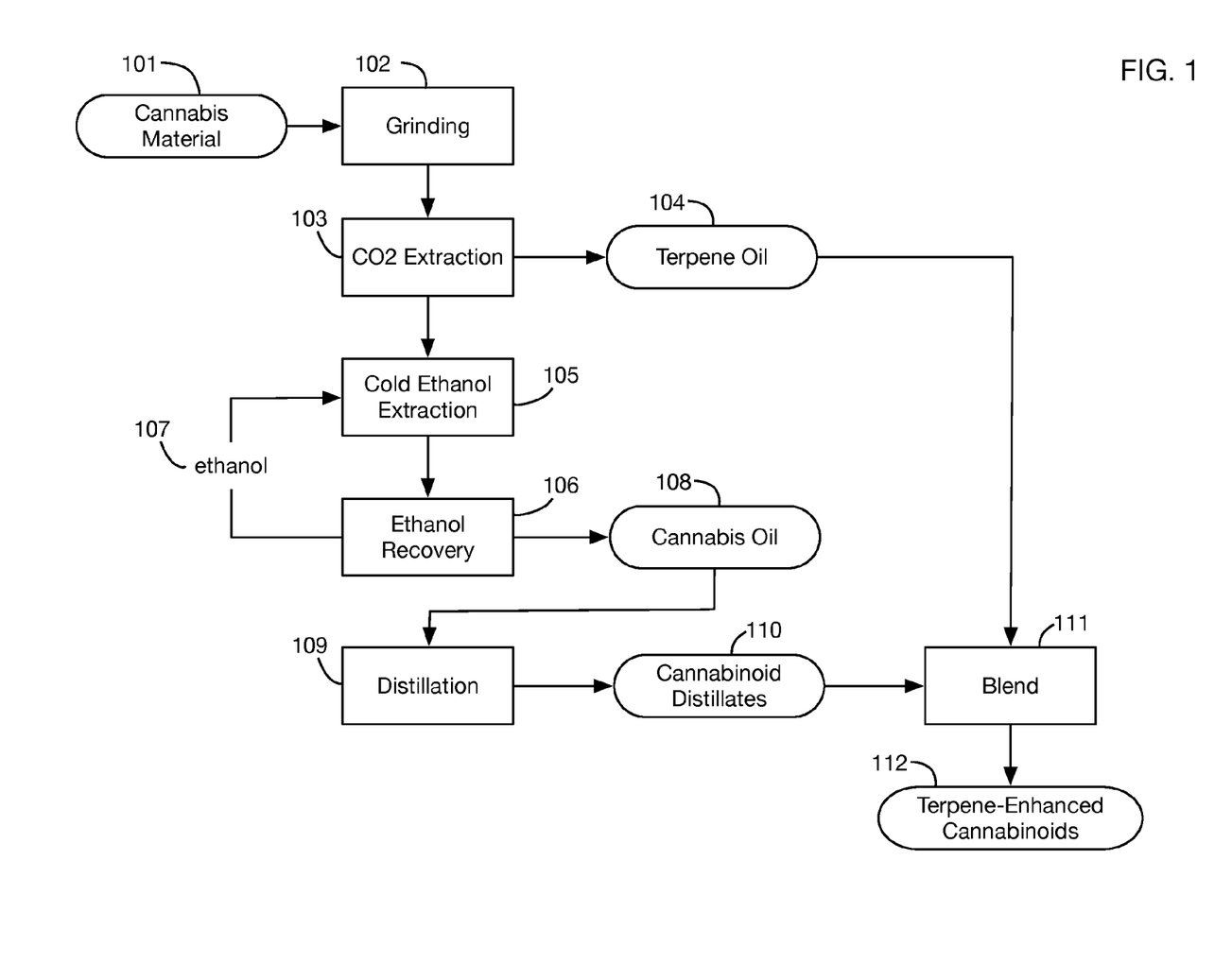
FIG. 1 shows a high-level flowchart of an embodiment of a method for producing a terpene-enhanced cannabinoid concentrate.

FIG. 1 shows a high-level flowchart of an embodiment of the invention. The steps shown are illustrative; one or more embodiments may use additional steps, or a subset of the steps shown. One or more embodiments may perform these steps in any desired order. One or more embodiments may perform one or more of these steps in parallel. The process shown in FIG. 1 generates a cannabinoid extract 112 that is enhanced with terpenes. Addition of terpenes to the cannabinoid extract may add flavor and may introduce compounds into the final blend that may have beneficial effects. The process may be performed at any scale, ranging for example from a micro scale such as on a benchtop to a large industrial scale such as in a refinery.

In the illustrative flowchart of FIG. 1, raw *cannabis* material 101 is obtained and is input into the grinding step 102. *Cannabis* material 101 may include for example, without limitation, the leaves, flowers, or buds of one or more *cannabis* plants. The flowers or buds have the highest concentration of cannabinoids and terpenes; however, any part or parts of the *cannabis* plant may be processed. The grinding step 102 may use any grinding method or methods, such as hand grinding, machine grinding, or use of a chipper or mulcher. In one or more embodiments, the grinding step may grind the material to a particle size similar to that of typical coffee grounds. Initial grinding may be followed in one or more embodiments by one or more filtering stages, for example to filter out stems or sticks. An illustrative mesh size used in one or more embodiments for filtering may be in the range of ¼ inch to ½ inch.

Grinding step 102 may be followed by CO2 extraction step 103. This step may be used for example to extract a terpene oil 104 from the ground plant material; some or all of this oil may be added back into the refined material in a later stage, as illustrated in blending step 111 in FIG. 1. CO2 extraction may for example extract terpenes more effectively and completely from *cannabis* material than the steam distillation process that is generally used for terpene extraction. CO2 extraction 103 may for example use a supercritical CO2 fluid. In this process CO2 is pressurized to form a liquid, and the liquid is mixed with the ground *cannabis* material to extract the desired compounds (in this case, terpenes). The CO2 may be removed from the solution by reducing the pressure, which allows the CO2 to evaporate as a gas and leaves the terpene extract behind. Illustrative process parameters used in one or more embodiments for the CO2 extraction step include: CO2 pressure in the range of 1000 psi to 1300 psi for the extraction; extraction temperature in the range of 80 F to 110 F; and separation temperature (after extraction) in the range of 40 F to 70 F. Run time for the CO2 extraction step may be for example in the range of 15 minutes to 6 hours.

After the extraction into the CO2 solution, terpene oils and hydrosols may be harvested from the solution. The oil may contain for example a mixture of terpenes and some cannabinoids, and the hydrosol may contain water-based terpenes and water. After removing the CO2 (via evaporation, for example), the remaining solution may be separated by allowing it to settle until the oil and the hydrosols separate, and then bleeding off the hydrosols. These products may then be filtered to remove waxes and cannabinoids by chilling them to a temperature in the range −80 F to 40 F, and then filtering with a coffee filter or a lower micron filter, for example with a pore size above 0.25 microns. Terpene oil 104 extracted in step 103 may be useful as a separate product (such as an essential oil), or it may be blended into further cannabinoid extracts in blending step 111.

Terpenes present in the extracted terpene oil and terpene hydrosol may include for example, without limitation, any or all of the terpenes alpha-Bisabolol, Camphene, 3-Carene, beta-Caryophyllene, Citronellol, Cymene, Eucalyptol, Famesene, Fenchol, Geraniol, Guaiol, Humulene, Isopropyltoluene, Isopulegol, Linalool, delta-Limonene, beta-Myrcene, Nerolidol, alpha-Pinene, Ocimene, alpha-Terpinene, gamma-Terpinene, and Terpinolene. Hydrosols may include primarily humelene and pinene, but any other terpenes may also be present in the hydrosols. Typical terpene concentration in hydrosols may be in the range of 1% to 10%, while typical terpene concentration in terpene oil may be up to 99%. Hydrosols and oil may also include some cannabinoids, for example up to 15% cannabinoids in terpene oils and up to 5% in hydrosols. The terpene oil and terpene hydrosols may be used for example as flavoring, or in aroma therapy products, in salves, in creams, or in topical treatments. These terpene compounds may have medicinal uses when taken internally or applied externally.

After extracting terpenes in step 103, the remaining non-extracted plant material may then be processed in cold ethanol extraction step 105. For example, the plant material that was exposed to the CO2 may be emptied from the CO2 extraction vessel and placed into one or more sanitary steel tubes, which may then be placed into a cryogenic freezer or other cooling apparatus to cool the plant material to a temperature in the range of −80 F to 30 F. Each tube may then be attached to a catch pot, possibly with a filter between the tube and the catch pot, and cold ethanol may be introduced into the tube and exposed to the plant material. After exposure, a dump valve may be opened to allow the cold ethanol solution to flow into the catch pot. A vacuum may also be applied to facilitate removal of the cold ethanol solution from the tube. The tube may be flushed for example for a time in the range of 5 minutes to 30 minutes. Flushing may continue for example until the ethanol stops or until it begins to turn greenish in color. The catch pot then contains an ethanol oil solution with extracted compounds from the plant material.

The ethanol oil solution may then be processed in ethanol recovery step 106 to remove some or all of the ethanol from the solution, leaving a *cannabis* oil product 108. As illustrated in FIG. 1, some or all of the recovered ethanol 107 may be recycled into the cold ethanol extraction step 105. The ethanol recovery process may for example use a vacuum distillation method to remove ethanol from the solution. The ethanol oil solution may be transferred into a recovery column which may be warmed in a water bath or in a jacketed column, for example to a temperature in the range of 120 F to 165 F. The recovery column may be connected to a condenser with circulating cold water and connected to a vacuum to accelerate ethanol evaporation. In an illustrative ethanol recovery process, after starting the cold water circulation the vacuum pump level may be set in the range of −10 inches Hg to −25 inches Hg. Condensed ethanol may be recovered into a container, which may then be used as input to the cold ethanol wash step for subsequent batches. Recovery run time may for example range from approximately 30 minutes to 3 hours, yielding recovered ethanol at a rate of approximately 7.5 L to 10 L per hour.

The remaining oil in the recovery column after the ethanol recovery step is an organic cannabinoid concentrated oil 108. This oil may be referred to colloquially (although not completely correctly) as "Rick Simpson Oil," or "RSO." It may contain for example cannabinoids in a concentration of approximately 50% to 90%, and may contain for example up to 20% terpenes. Cannabinoids contained in the oil may include for example, without limitation, THCa, THC, THCV, CBDa, CBD, CBC, CBG, and CBN. The oil may be processed further to form a concentrate (as described below), or it may be used directly as a final product. The oil may be smoked or vaped, for example as a "shatter" or in a vape pen as an oil. It may be activated, for example by heating in an oven to approximately 180 F, and incorporated into edible products, topicals, creams, or salves.

The *cannabis* oil 108 may then be further concentrated in distillation step 109. Distillation 109 may for example use any distillation devices and techniques, including for example, without limitation, short path distillation, thin film distillation, wipe film distillation, and spinning band distillation. An illustrative distillation process is as follows. The *cannabis* oil 108 is placed on a hot plate with a stir rod or stir bar, at a temperature of no more than 140 C in one or more embodiments. Distillation may be performed under vacuum or without vacuum. With a vacuum under 5 torr, most terpenes distill out before 157 C; cannabinoid distillates 110 distill out between 157 C and 185 C; and some additional products such as CBG, CBN, and THCV distill out between 185 C and 230 C. Without a vacuum, distillation may be performed for example between 370 C and 440 C. In one or more embodiments, the products of distillation may be redistilled, possibly multiple times, to increase the concentration of the final product. The cannabinoid distillates 110 may for example have cannabinoid concentrations between 80% and 99.99%, with higher levels possible using multiple distillations. Cannabinoid distillates may be smoked or vaped, for example as a "shatter" or in a vape pen as an oil. They are already activated as a result of the distillation process; therefore, they may be incorporated into edible products, topicals, creams, or salves.

In one or more embodiments, the cannabinoid distillates 110 may be blended in step 111 with the terpene oil 104 extracted using CO2 extraction 103, to create a terpene-enhanced cannabinoid concentrate 112. This blending may for example add flavor and may create additional effects when smoking, vaping, or ingesting the blend. Blending terpene oil with the cannabinoid distillates may also make the product 112 thin enough to be used in vape pens. In one or more embodiments, the blending step 111 may use a ratio by volume of terpene oil to cannabinoid distillates in the range 1:25 to 1:5. An illustrative embodiment may use for example a ratio of terpene oil to cannabinoid distillates of 1:10.

Figure 2:
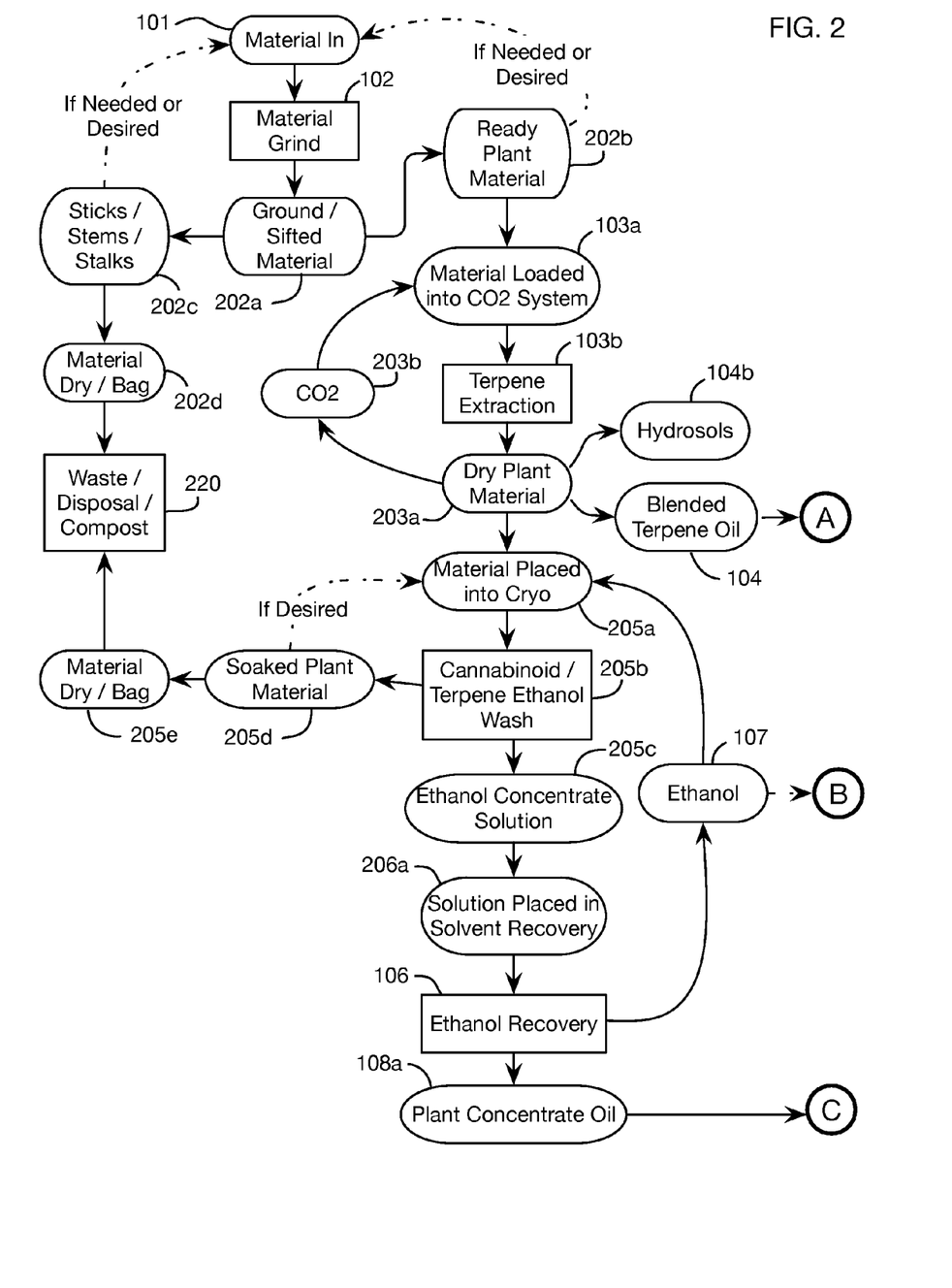
FIGS. 2 and 3 show a detailed flowchart of an embodiment of the invention, illustrating steps, products, and optional flow paths in the process.
Figure 3:
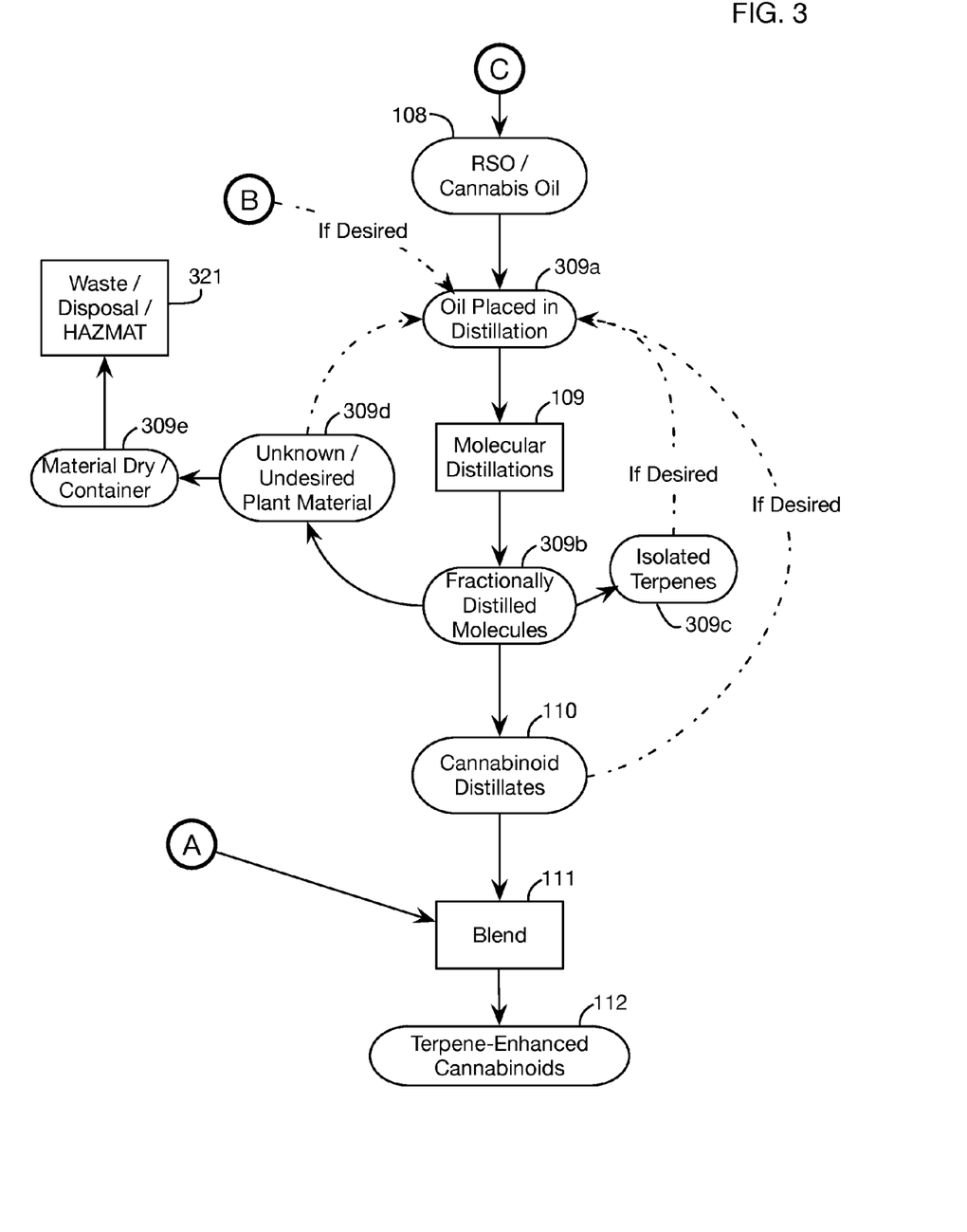

FIGS. 2 and 3 show a more detailed flowchart of an embodiment of the invention. (FIG. 3 is a continuation of FIG. 2). *Cannabis* material 101 is input into grinding step 102, yielding ground/sifted material 202*a*. This material 202*a* is then filtered to remove sticks, stems, and stalks 202*c*. The remaining ready plant material 202*b* is input into the CO2 extraction process. If needed or desired, additional grinding, sifting, and filtering may be performed on either or both of the sticks, stems, and stalks 202*c*, and the ready plant material 202*b*, prior to CO2 extraction. Unused stems, sticks and stalks 202*c* are dried and bagged into waste products 202*c*, and sent to a waste disposal/composting process 220.

The material 202*b* is then loaded into a CO2 extraction vessel, forming loaded material 103*a*. Terpene extraction 103*b* is then performed using CO2 203*b* as a solvent. This extraction yields terpene oil 104 and terpene hydrosols 104*b*. The remaining dry plant material 203*a* is further processed with the next steps in the process. CO2 203*b* removed from the solution may be recycled and used for additional terpene extraction steps 103*b*.

The cold ethanol extraction process then proceeds with dry plant material 203*a* placed into a container and cryogenically frozen, yielding frozen material 205*a*. Ethanol wash 205*b* is then performed over this frozen material, yielding ethanol concentrate solution 205*c*. The remaining soaked plant material 205*d* may be reprocessed with additional cryogenic freezing 205*a* and ethanol wash 205*b* if desired, or formed into waste material 205*e* that is transmitted to waste disposal/composting process 220. The solution 205*c* is then transferred to a solvent recovery vessel 206*a*, and ethanol recovery process 106 removes ethanol 107 from the solution. The ethanol may be recycled if desired for subsequent cold ethanol extraction steps. After removing ethanol, the solution contains plant concentrate oil 108*a*.

Turning now to FIG. 3, which is a continuation of FIG. 2, plant concentrate oil 108*a* ("C" from FIG. 2) may be used directly as *cannabis* oil 108 (also referred to colloquially as "RSO"). It may also be further processed with distillation and blending. Oil 108 may be placed in a distillation vessel 309*a*. In addition, if desired, some or all of the ethanol 107 removed from the oil ("B" from FIG. 2) may be further distilled to obtain any residual cannabinoids or other products. Molecular distillation steps 109 may yield various fractionally distilled products 309*b* (for example at different distillation temperatures), including cannabinoid distillates 110 and isolated terpenes 309a. Remaining plant material 309d after distillation to extract products 110 and 309c may be transformed into waste 309e and disposed in step 321, or it may be redistilled. Products 110 and 309c may also be redistilled, for example to increase product concentration. Cannabinoid distillates 110 may then be blended with the terpene oil 104 from CO extraction ("A" from FIG. 1), yielding terpene-enhanced cannabinoid oil 112.

Figure 4:
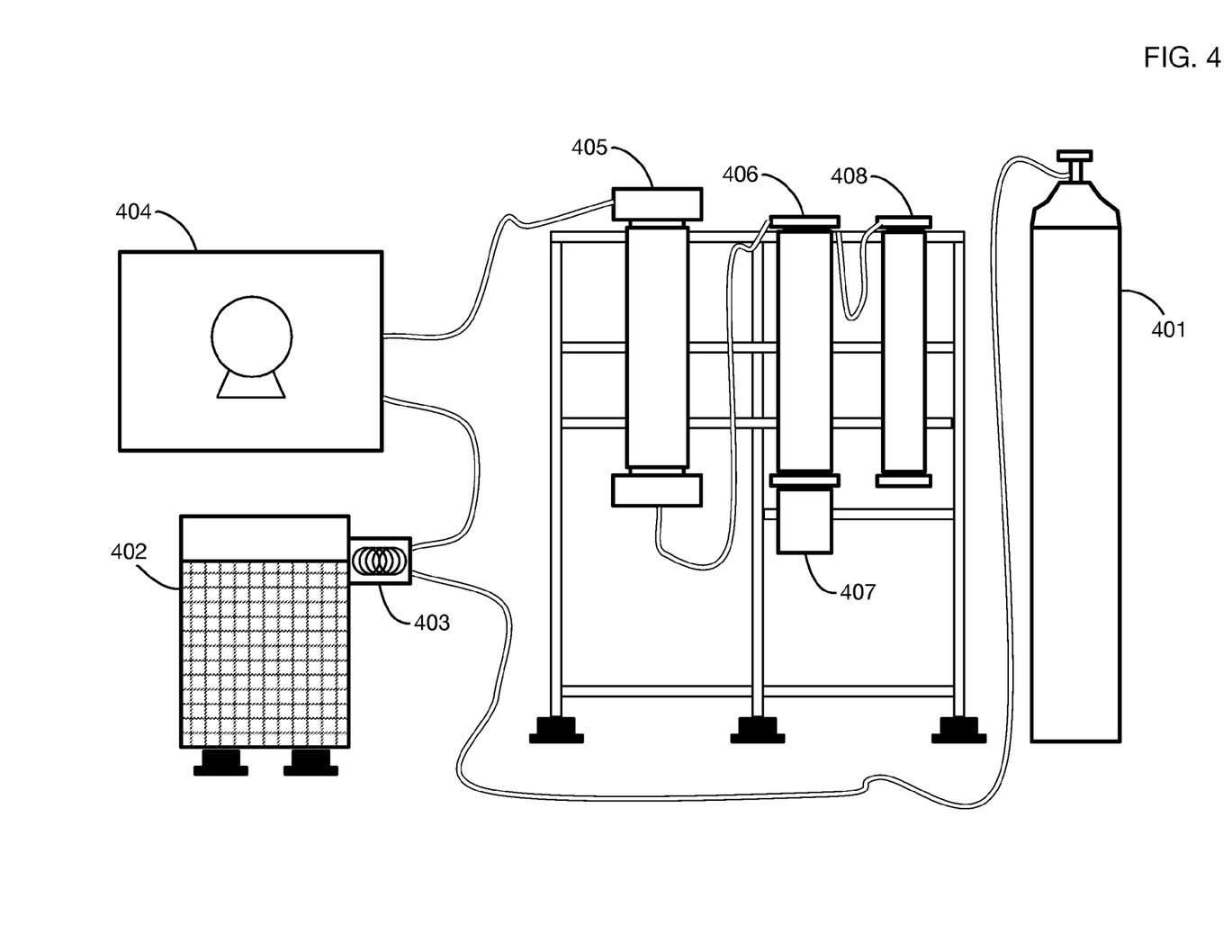
FIG. 4 shows illustrative equipment that may be used in the CO2 extraction step of the process of FIG. 1.

FIGS. 4 through 9 show illustrative equipment that may be used in one or more steps of the process in one or more embodiments of the invention. This equipment is illustrative; one or more embodiments may use any desired equipment for any step or steps. Any of the steps may be manual, automated, or semi-automated. FIG. 4 shows illustrative equipment that may be used for CO2 extraction in one or more embodiments of the invention. CO2 extraction may for example use an Apeks® 1500-20 L Botanical Oil Extraction System, or any similar equipment. FIG. 4 shows selected components of the system; it does not show all components and all connections. CO2 gas is obtained from CO2 tank 401. This gas flows to chiller 402, which cools the gas using heat exchanger 403. The pressure of the gas is increased with compression pump 404, yielding a supercritical CO2 fluid. This fluid is passed over ground and frozen *cannabis* material in extraction vessel 405. The CO2 solution with extracted terpenes then flows to separation vessel 406, which has a collection cup 407 at the bottom. The CO2 evaporates from vessel 406, leaving the terpene oil and hydrosols in collection cup 407. If desired or needed, further separation may be performed using separation vessel 408.

Figure 5:
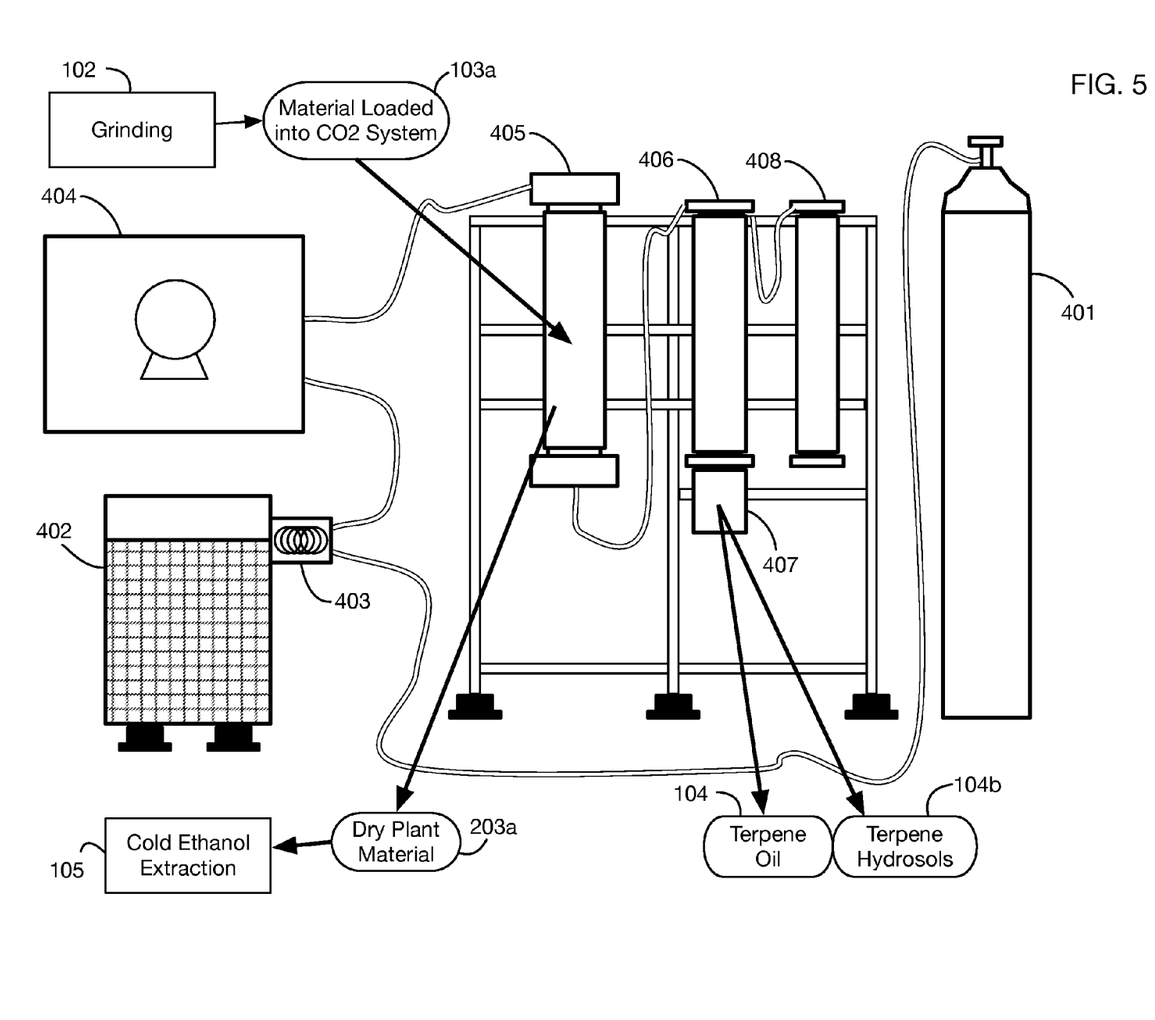
FIG. 5 shows how the equipment of FIG. 4 relates to selected steps and products shown in the process flowchart of FIGS. 2 and 3.

FIG. 5 annotates the equipment of FIG. 4 with selected process steps and products from the flowchart of FIGS. 2 and 3. After grinding 102, material 103a is loaded into the CO2 system in extraction vessel 405. The products of CO2 extraction including terpene oil 104 and terpene hydrosols 104b are collected in collection cub 407. After CO2 extraction, the plant material 203a remaining in vessel 405 is removed and is transferred to cold ethanol extraction step 105, which is described next.

Figure 6:
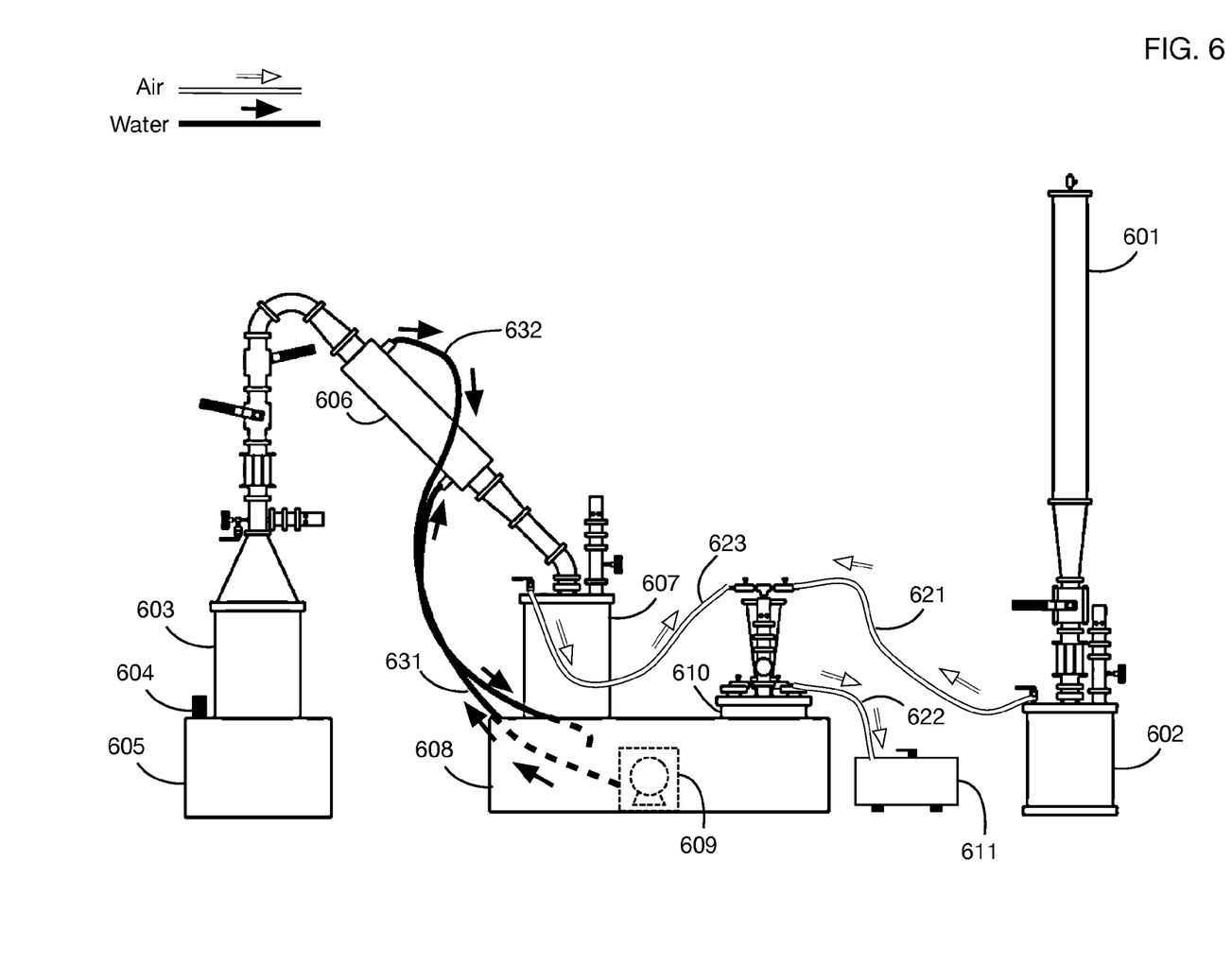
FIG. 6 shows illustrative equipment that may be used in the cold ethanol extraction and ethanol recovery steps of the process of FIG. 1.

FIG. 6 shows illustrative equipment that may be used for cold ethanol extraction in one or more embodiments of the invention. Frozen plant material is placed into tube 601, which is flushed with cold ethanol. The cold ethanol solution containing extracted compounds is drained into receiving vessel 602, assisted by a vacuum. The vacuum pump 611 pulls air through line 621 to a connection at the top of vacuum cold trap 610, and from the cold trap through line 622 to the pump. The ethanol solution is then transferred to container 603, which is placed into hot water bath 605. The hot water bath is heated by heating element 604. The heat causes the ethanol in the solution to evaporate; ethanol vapor reaches condenser 606 which is cooled by cold water flowing from cold solution bath 608 through water line 631, and then returned via line 632 to the cold bath 608. Water flow is driven by pump 609 in the cold solution bath. Distillation of ethanol is vacuum assisted with vacuum line 623 attached to receiving vessel 607 that collects condensed ethanol. An additional vacuum cold trap 610 captures residual ethanol that may be in the vacuum line.

Figure 6A:
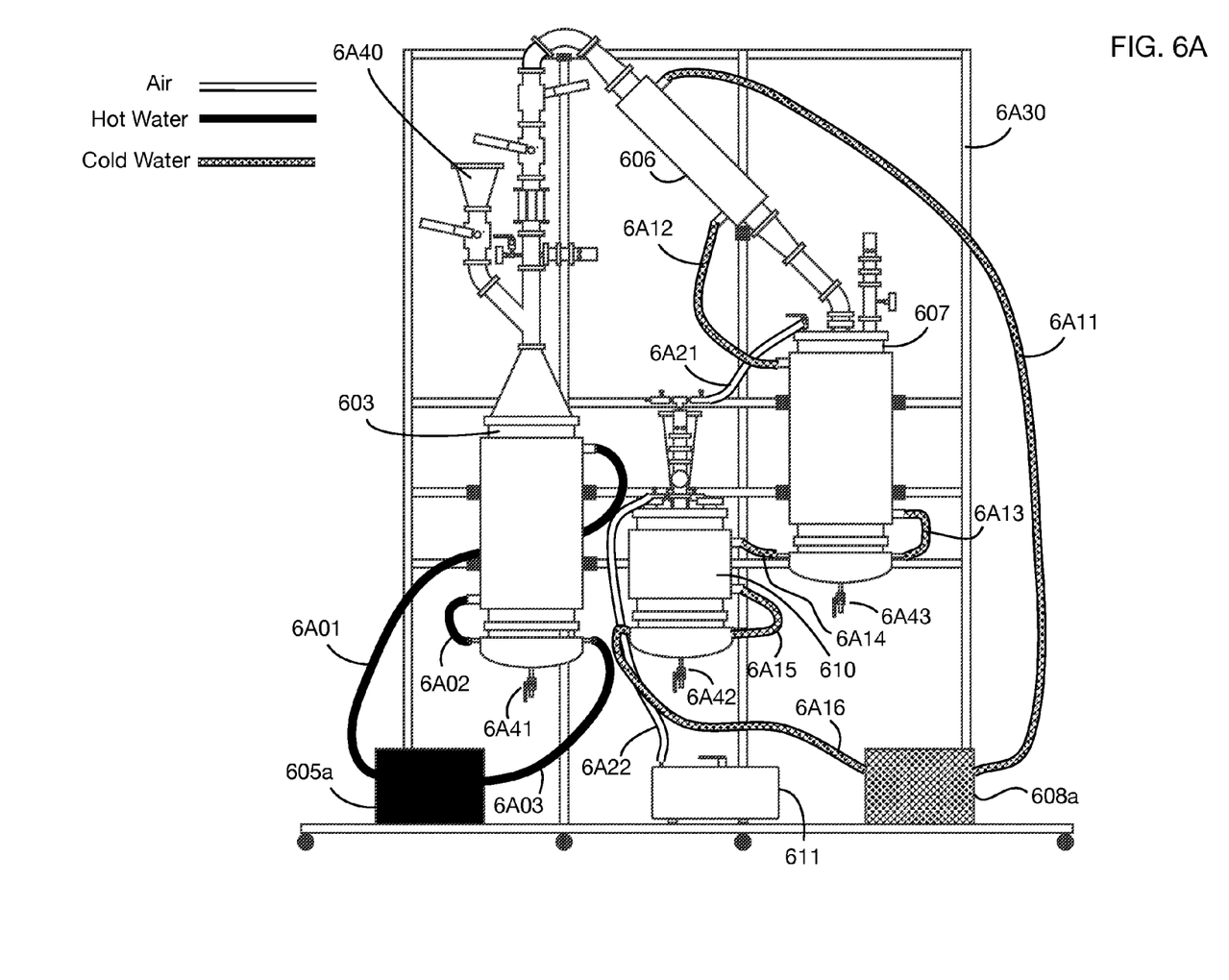
FIG. 6A shows a variation of the illustrative equipment of FIG. 6 for ethanol recovery.

FIG. 6A shows another embodiment of equipment that may be used for ethanol recovery. In this embodiment, the equipment is mounted on rack 6A30, for example to comply with building and health codes. The equipment arrangement in FIG. 6A may also support more efficient operation than the arrangement of FIG. 6; for example, a batch of material may be processed using the embodiment of FIG. 6A in approximately 10 minutes, as compared to approximately an hour using the equipment configuration of FIG. 6. Efficiency improvements are achieved for example by providing mechanisms for the input of material and output of products without requiring equipment to be disassembled, reassembled, moved, or transferred. For example, the embodiment of FIG. 6A adds a feed spout 6A40 for container 603, so that users can add more material to the oil base without having to dismantle equipment. It also adds jacketed collection bottoms to each of the collection bases, which allows for material harvesting directly off the system without disassembling the equipment. A spout is attached to each collection bottom for harvesting of material: spout 6A41 may be used for harvesting of oil from collection vessel 603; spout 6A42 may be used for harvesting of ethanol from vacuum cold trap 610; and spout 6A43 may be used for harvesting of ethanol from recovered ethanol receiving vessel 607.

As in the embodiment of FIG. 6, an ethanol solution added to container 603 after frozen plant material has been washed with cold ethanol to extract plant compounds into the ethanol solution. In the embodiment shown in FIG. 6, container 603 is placed in a hot water bath. In the embodiment shown in FIG. 6A, a separate hot water reservoir 605a is used and hot water is pumped along water lines to a jacket surrounding container 603, thereby heating the ethanol solution and generating ethanol vapors that are recovered. For example, in the embodiment shown in FIG. 6A, hot water flows from reservoir 605a along water line 6A01 to a jacket surrounding container 603, and then along water line 6A02 to a jacket surrounding the collection bottom of container 603, and then along water line 6A03 back to the hot water reservoir 605a. As in the embodiment of FIG. 6, ethanol vapors reach condenser 606, and condensed ethanol flows to recovered ethanol receiving vessel 607. In the embodiment of FIG. 6, receiving vessel 607 is placed in a cold water bath. In the embodiment shown in FIG. 6A, a separate cold water reservoir 608a is used. Cold water is pumped along water lines from reservoir 608a to the condenser and to a jacket surrounding the ethanol receiver. Also as in FIG. 6, there may be an additional vacuum cold trap 610 to capture residual ethanol that may be in the vacuum line, but in FIG. 6A this vacuum cold trap receives cold water along water lines rather than being placed directly in a cold water bath. In the embodiment of FIG. 6A, cold water flows along water line 6A11 from the cold water reservoir 608a to the condenser 606, then along line 6A12 to a jacket surrounding recovered ethanol receiving vessel 607. The cold water then flows along line 6A13 to a jacket surrounding the collection bottom of the receiving vessel 607. Cold water then flows along line 6A14 to a jacket surrounding vacuum cold trap 610, then along line 6A15 to a jacket surrounding the collection bottom of the vacuum cold trap, and then along line 6A16 to return to the cold water reservoir 608a. Vacuum pump 611 provides a vacuum, with vacuum lines 6A22 and 6A21 connecting the vacuum pump to the vacuum cold trap 610 and to the recovered ethanol receiving vessel 607. The specific configuration and routing of the air and water lines shown in FIG. 6A are illustrative; one or more embodiments may route and configure these lines in any desired manner. One or more embodiments may use continuous sources of hot or cold water instead of or in addition to water reservoirs as illustrated in FIG. 6A.

Figure 7:
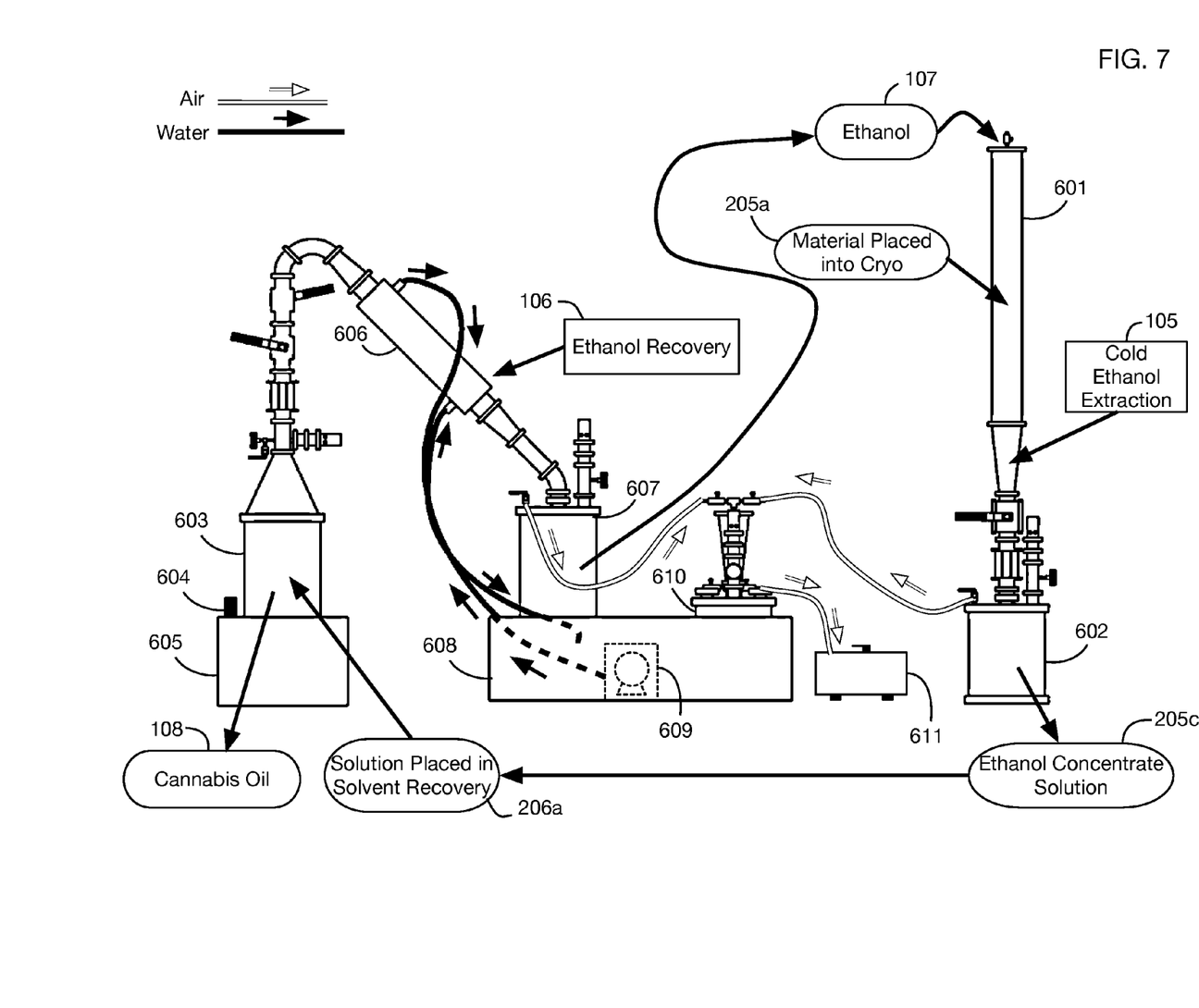
FIG. 7 shows how the equipment of FIG. 6 relates to selected steps and products shown in the process flowchart of FIGS. 2 and 3.

FIG. 7 annotates the equipment of FIG. 6 with selected process steps and products from the flowchart of FIGS. 2 and 3. Material 205a that is cryogenically frozen is placed into tube 601. Ethanol 107 is added to the tube and cold ethanol extraction step 105 removes the ethanol concentrate solution 205c from tube 601 into receiving container 602. This solution 205c is then transferred to container 603 as solution 206a for solvent (ethanol) recovery. Ethanol recovery step 106 occurs in condenser 606 (and possibly in vacuum cold trap 610 as well) as ethanol vapor condenses, and recovered ethanol is collected in container 607 (and possibly in container 610). This recovered ethanol 107 may be recycled for additional cold ethanol flushes of material in tube 601. The material remaining in container 603 after ethanol recovery is *cannabis* oil 108.

Figure 8:
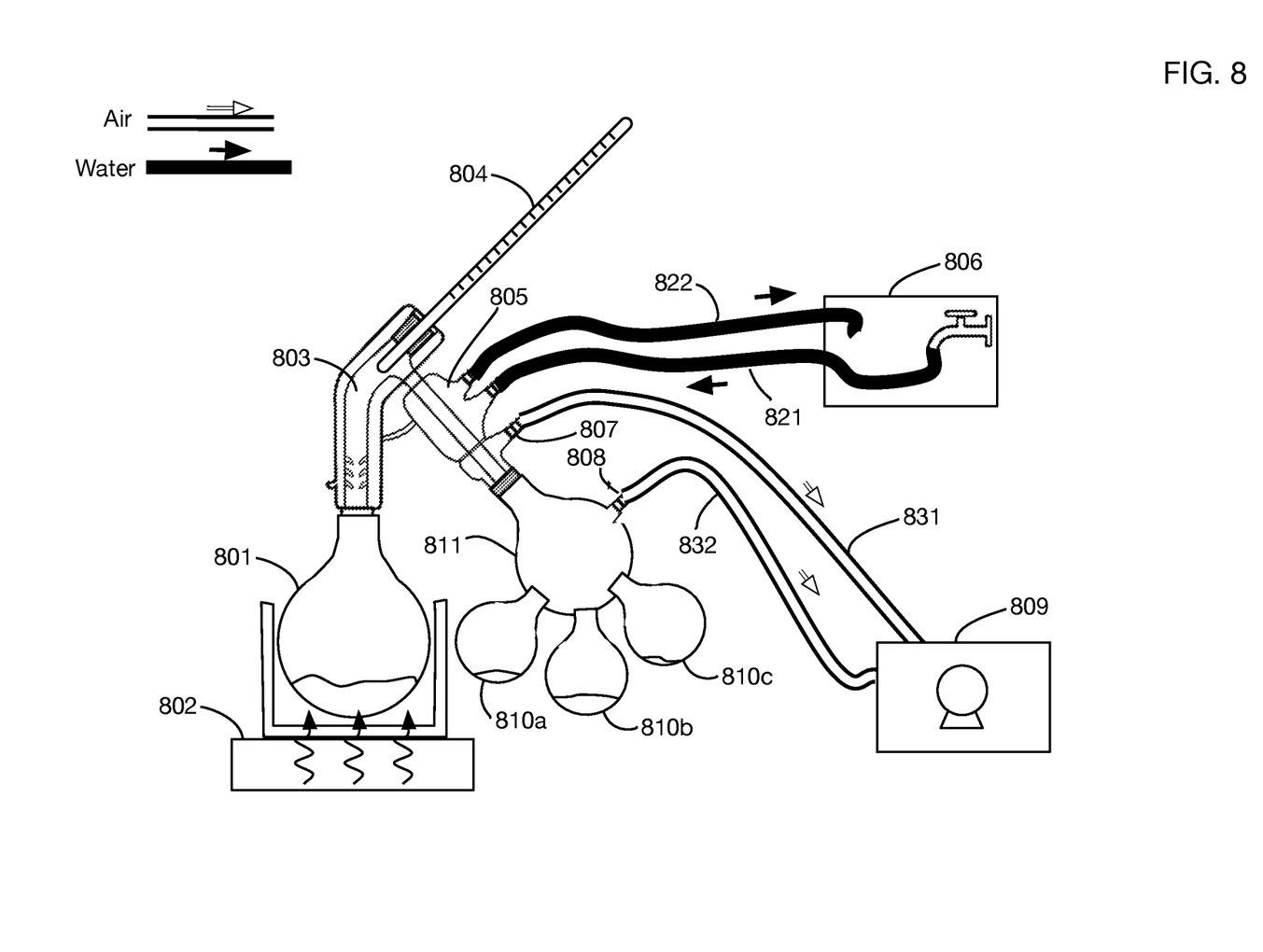
FIG. 8 shows illustrative equipment that may be used in the distillation step of the process of FIG. 1.

FIG. 8 shows illustrative equipment that may be used for *cannabis* oil distillation in one or more embodiments of the invention. This figure shows a short path distillation process; one or more embodiments may use any desired distillation process, including but not limited to short path distillation. Flask 801 containing *cannabis* oil is placed on heating element 802. Distillation head 803 attached to flask 801 has an attached thermometer 804, and has connections for vacuum and water. Water line 821 provides cooling water to the condenser water jacket 805 from water source 806, and return water line 822 drains or recirculates this water. Vacuum line 831 attaches connection 807 to vacuum pump 809, and vacuum line 832 attaches to connection 808 on distribution bulb 811. In this illustrative embodiment, three collection flasks 810a, 810b, and 810c are attached to distribution bulb 811.

Figure 9:
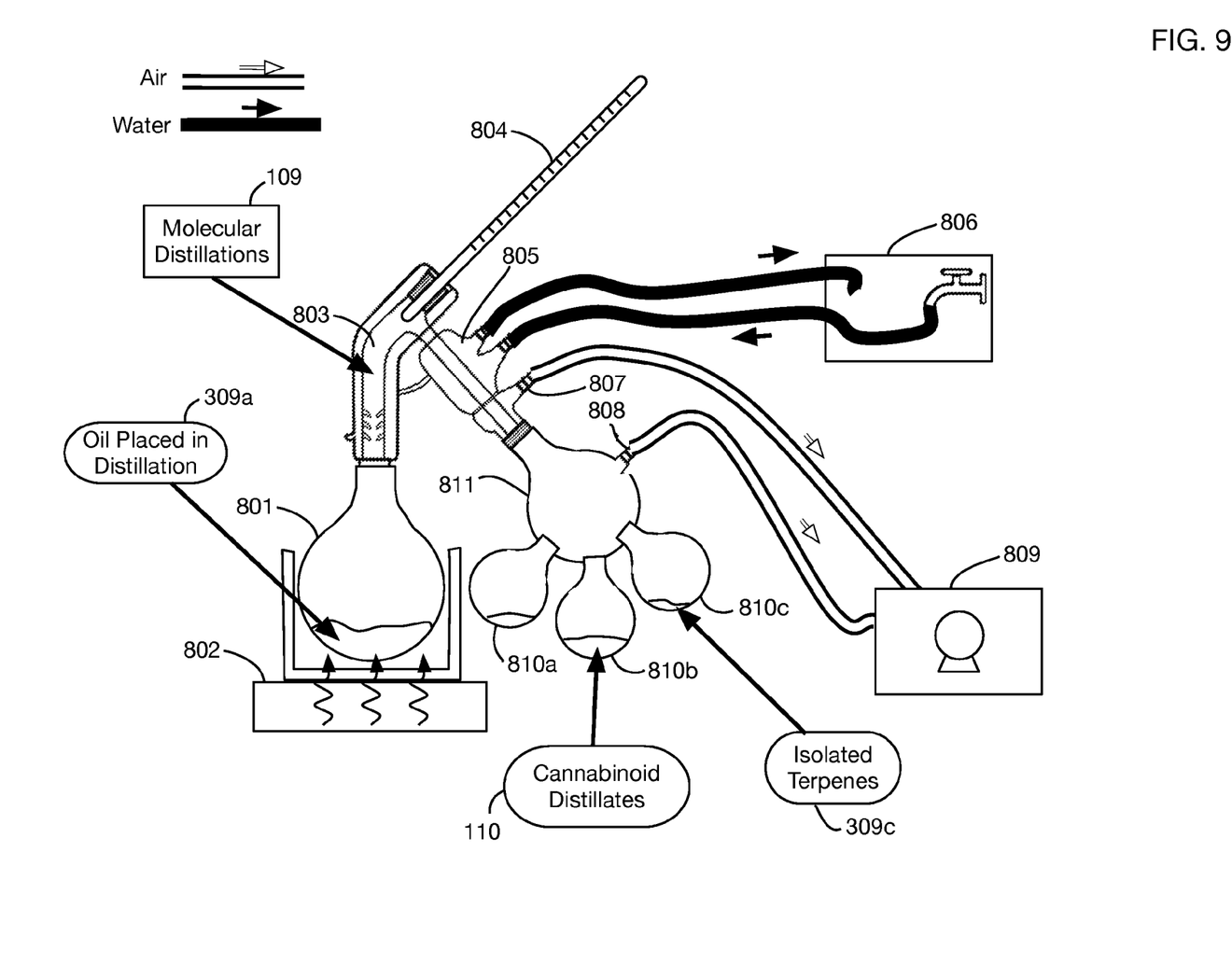
FIG. 9 shows how the equipment of FIG. 8 relates to selected steps and products shown in the process flowchart of FIGS. 2 and 3.

FIG. 9 annotates the equipment of FIG. 8 with selected process steps and products from the flowchart of FIGS. 2 and 3. *Cannabis* oil placed in distillation 309a is placed in flask 801. Molecular distillations 109 occur in distribution head 803, and distillation products such as cannabinoid distillates 110 and isolated terpenes 309c are collected in collection flasks 810a, 810b, or 810c. Thermometer 804 may be used to monitor the distillation temperature in order to separate and identify products such as cannabinoid distillates 110 and terpene distillates 309c that distill out at different temperatures.

While the invention herein disclosed has been described by means of specific embodiments and applications thereof, numerous modifications and variations could be made thereto by those skilled in the art without departing from the scope of the invention set forth in the claims.

What is claimed is:

1. An apparatus that produces a terpene-enhanced cannabinoid concentrate comprising:
    a grinder configured to grind *cannabis* to produce ground *cannabis*;
    a carbon dioxide tank containing a carbon dioxide gas;
    a chiller comprising a heat exchanger, wherein said chiller is configured to cool said carbon dioxide gas to form a cooled carbon dioxide gas;
    a compression pump configured to compress said cooled carbon dioxide gas to form a carbon dioxide solvent, wherein said carbon dioxide solvent comprises a supercritical carbon dioxide fluid;
    an extraction vessel configured to receive said ground *cannabis* and said supercritical carbon dioxide fluid, and configured to pass said supercritical carbon dioxide fluid over said ground *cannabis* to form a carbon dioxide solution;
    a separation vessel comprising a collection cup and configured to
        receive said carbon dioxide solution;
        separate said carbon dioxide solution into carbon dioxide and terpene oil and terpene hydrosol; and,
        collect said terpene oil and said terpene hydrosol in said collection cup;
    a freezer configured to freeze residual ground *cannabis* to obtain a frozen residual;
    a tube into which said frozen residual is placed and into which cold ethanol is flushed to produce an ethanol oil solution;
    an ethanol oil solution receiving vessel coupled to said tube and configured to receive said ethanol oil solution;
    a vacuum pump;
    a vacuum line coupled to said ethanol oil solution receiving vessel and to said vacuum pump;
    a separator configured to separate said ethanol oil solution into recovered ethanol and *cannabis* oil;
    a distiller configured to distill at least a portion of said *cannabis* oil to obtain cannabinoid distillates; and,
    a blender configured to blend said cannabinoid distillates with said terpene oil to obtain the terpene-enhanced cannabinoid concentrate.

2. The apparatus of claim 1 further comprising:
    means for pressurizing said carbon dioxide solvent to form said supercritical carbon dioxide fluid;
    means for exposing said ground *cannabis* to said supercritical carbon dioxide fluid to obtain a carbon dioxide extraction solution;
    means for reducing a pressure of said carbon dioxide extraction solution to remove said carbon dioxide solvent, and obtaining a carbon dioxide extraction product;
    means for separating said carbon dioxide extraction product into said terpene oil and said terpene hydrosol; and,
    means for filtering said terpene oil and said terpene hydrosol from one another.

3. The apparatus of claim 1 further comprising:
    said compression pump configured to pressurize said carbon dioxide solvent to form said supercritical carbon dioxide fluid;
    said extraction vessel configured to expose said ground *cannabis* to said supercritical carbon dioxide fluid to obtain a carbon dioxide extraction solution;
    a valve configured to reduce a pressure of said carbon dioxide extraction solution to remove said carbon dioxide solvent to obtain a carbon dioxide extraction product;
    said separator configured to separate said carbon dioxide extraction product into said terpene oil and said terpene hydrosol; and,
    a filter that is configured to filter said terpene oil and said terpene hydrosol from one another.

4. The apparatus of claim 1 wherein said separator configured to separate said ethanol oil solution into said recovered ethanol and said *cannabis* oil comprises
    a container into which said ethanol oil solution is placed;
    means for heating said container;
    an ethanol condenser coupled to said container and configured to receive vapors from said container;
    means for cooling said ethanol condenser;
    a recovered ethanol receiving vessel coupled to said ethanol condenser, and configured to receive said recovered ethanol;
    means for cooling said recovered ethanol receiving vessel;
    said vacuum pump; and,
    said vacuum line coupled to said vacuum pump and to said recovered ethanol receiving vessel.

5. The apparatus of claim 1 wherein said separator configured to separate said ethanol oil solution into said recovered ethanol and said *cannabis* oil comprises
    a container into which said ethanol oil solution is placed;

a heater configured to heat said container;
an ethanol condenser coupled to said container and configured to receive vapors from said container;
an ethanol condenser cooler configured to cool said ethanol condenser;
a recovered ethanol receiving vessel coupled to said ethanol condenser, and configured to receive said recovered ethanol;
a recovered ethanol receiving vessel cooler configured to cool said recovered ethanol receiving vessel;
said vacuum pump; and,
said vacuum line coupled to said vacuum pump and to said recovered ethanol receiving vessel.

6. The apparatus of claim 5 wherein said separator configured to separate said ethanol oil solution into said recovered ethanol and said *cannabis* oil further comprises
a vacuum cold trap connected between said recovered ethanol receiving vessel and said vacuum pump, and configured to collect residual ethanol in said vacuum line; and,
a vacuum cold trap cooler configured to cool said vacuum cold trap.

7. The apparatus of claim 6 wherein
said heater configured to heat said container comprises a hot water bath into which said container is placed, wherein said hot water bath is heated by a heating element;
said ethanol condenser cooler configured to cool said ethanol condenser comprises
a cold solution bath containing cold water;
a water line coupled to said cold solution bath and to said ethanol condenser;
said recovered ethanol receiving vessel cooler configured to cool said recovered ethanol receiving vessel comprises said cold solution bath; and,
said vacuum cold trap cooler configured to cool said vacuum cold trap comprises said cold solution bath.

8. The apparatus of claim 6 further comprising:
a rack onto which said container, said recovered ethanol receiving vessel, and said vacuum cold trap are mounted.

9. The apparatus of claim 8 further comprising:
a feed spout coupled to said container and configured to receive said ethanol oil solution;
a *cannabis* oil collection bottom coupled to said container;
a *cannabis* oil spout coupled to said *cannabis* oil collection bottom;
a recovered ethanol collection bottom coupled to said recovered ethanol receiving vessel;
a recovered ethanol spout coupled to said recovered ethanol collection bottom;
a residual ethanol collection bottom coupled to said vacuum cold trap; and,
a residual ethanol spout coupled to said residual ethanol collection bottom.

10. The apparatus of claim 9 wherein
said heater configured to heat said container comprises
a hot water reservoir;
one or more hot water circulation lines coupled to said hot water reservoir, to a container jacket surrounding said container, and to a *cannabis* oil collection bottom jacket surrounding said *cannabis* oil collection bottom;
said ethanol condenser cooler configured to cool said ethanol condenser comprises
a cold water reservoir;
one or more cold water circulation lines coupled to said cold water reservoir, and to an ethanol condenser jacket surrounding said ethanol condenser;
said recovered ethanol receiving vessel cooler configured to cool said recovered ethanol receiving vessel comprises
said cold water reservoir;
a second set of one or more cold water circulation lines coupled to said cold water reservoir, to a recovered ethanol receiving vessel jacket surrounding said recovered ethanol receiving vessel, and to a recovered ethanol collection bottom jacket surrounding said recovered ethanol collection bottom;
said vacuum cold trap cooler configured to cool said vacuum cold trap comprises
said cold water reservoir;
a third set of one or more cold water circulation lines coupled to said cold water reservoir, to a vacuum cold trap jacket surrounding said vacuum cold trap, and to a residual ethanol collection bottom jacket surrounding said residual ethanol collection bottom.

11. The apparatus of claim 1 further comprising:
means for generating a vacuum in a distillation vessel;
means for heating said *cannabis* oil; and,
means for collecting a condensed vapor as said cannabinoid distillates.

12. The apparatus of claim 1 further comprising:
a vacuum generator configured to generate a vacuum in a distillation vessel;
a heater configured to heat said *cannabis* oil; and,
a collector configured to collect a condensed vapor as said cannabinoid distillates.

13. The apparatus of claim 1 wherein said distiller configured to distill at least a portion of said *cannabis* oil to obtain said cannabinoid distillates comprises:
a heating element;
a flask placed on said heating element, wherein said at least a portion of said *cannabis* oil is placed in said flask;
a distillation head coupled to said flask;
a cannabinoid distillates condenser coupled to said distillation head;
a water jacket surrounding said cannabinoid distillates condenser;
a water line coupled to said water jacket;
said vacuum pump;
said vacuum line coupled to said vacuum pump and to said cannabinoid distillates condenser; and,
one or more collection flasks coupled to said cannabinoid distillates condenser and configured to receive said cannabinoid distillates.

14. The apparatus of claim 1 further comprising:
means for redistilling said cannabinoid distillates to obtain higher concentration cannabinoid distillates; and,
means for blending said higher concentration cannabinoid distillates with said terpene oil to obtain said terpene-enhanced cannabinoid concentrate.

15. The apparatus of claim 1 further comprising:
a redistiller configured to redistill said cannabinoid distillates to obtain higher concentration cannabinoid distillates; and,
said blender further configured to blend said higher concentration cannabinoid distillates with said terpene oil to obtain said terpene-enhanced cannabinoid concentrate.

16. The apparatus of claim 1 wherein a ratio by volume of said terpene oil to said cannabinoid distillates in said terpene-enhanced cannabinoid concentrate is in the range 1:25 to 1:5.

17. An apparatus that produces a terpene-enhanced cannabinoid concentrate comprising:
- a grinder configured to grind *cannabis* to produce ground *cannabis*;
- a carbon dioxide tank containing a carbon dioxide gas;
- a chiller comprising a heat exchanger, wherein said chiller is configured to cool said carbon dioxide gas to form a cooled carbon dioxide gas;
- a compression pump configured to compress said cooled carbon dioxide gas to form a carbon dioxide solvent, wherein said carbon dioxide solvent comprises a supercritical carbon dioxide fluid;
- an extraction vessel configured to receive said ground *cannabis* and said supercritical carbon dioxide fluid, and configured to pass said supercritical carbon dioxide fluid over said ground *cannabis* to form a carbon dioxide solution;
- a separation vessel comprising a collection cup and configured to
  - receive said carbon dioxide solution;
  - separate said carbon dioxide solution into carbon dioxide and terpene oil and terpene hydrosol;
  - collect said terpene oil and said terpene hydrosol in said collection cup;
- a freezer configured to freeze residual ground *cannabis* from said extraction vessel to obtain a frozen residual;
- a tube into which said frozen residual is placed and into which cold ethanol is flushed to produce an ethanol oil solution;
- an ethanol oil solution receiving vessel coupled to said tube and configured to receive said ethanol oil solution;
- a vacuum pump;
- a vacuum line coupled to said ethanol oil solution receiving vessel and to said vacuum pump;
- a container into which said ethanol oil solution is placed;
- an ethanol condenser coupled to said container and configured to receive vapors from said container;
- a recovered ethanol receiving vessel coupled to said ethanol condenser, and configured to receive recovered ethanol;
- a second vacuum line coupled to said vacuum pump and to said recovered ethanol receiving vessel;
- a vacuum cold trap connected between said recovered ethanol receiving vessel and said vacuum pump, and configured to collect residual ethanol in said second vacuum line;
- a rack onto which said container, said recovered ethanol receiving vessel, and said vacuum cold trap are mounted;
- a feed spout coupled to said container and configured to receive said ethanol oil solution;
- a *cannabis* oil collection bottom coupled to said container;
- a *cannabis* oil spout coupled to said *cannabis* oil collection bottom;
- a recovered ethanol collection bottom coupled to said recovered ethanol receiving vessel;
- a recovered ethanol spout coupled to said recovered ethanol collection bottom;
- a residual ethanol collection bottom coupled to said vacuum cold trap;
- a residual ethanol spout coupled to said residual ethanol collection bottom;
- a hot water reservoir;
- one or more hot water circulation lines coupled to said hot water reservoir, to a jacket surrounding said container, and to a jacket surrounding said *cannabis* oil collection bottom;
- a cold water reservoir;
- one or more cold water circulation lines coupled to said cold water reservoir, and to a jacket surrounding said ethanol condenser;
- a second set of one or more cold water circulation lines coupled to said cold water reservoir, to a jacket surrounding said recovered ethanol receiving vessel, and to a jacket surrounding said recovered ethanol collection bottom;
- a third set of one or more cold water circulation lines coupled to said cold water reservoir, to a jacket surrounding said vacuum cold trap, and to a jacket surrounding said residual ethanol collection bottom;
- a heating element;
- a flask placed on said heating element, wherein at least a portion of *cannabis* oil from said container is placed in said flask;
- a distillation head coupled to said flask;
- a cannabinoid distillates condenser coupled to said distillation head;
- a water jacket surrounding said cannabinoid distillates condenser;
- a water line coupled to said water jacket;
- a third vacuum line coupled to said vacuum pump and to said cannabinoid distillates condenser;
- one or more collection flasks coupled to said cannabinoid distillates condenser and configured to receive cannabinoid distillates; and,
- a blender configured to blend said cannabinoid distillates with said terpene oil to obtain the terpene-enhanced cannabinoid concentrate.

* * * * *